(12) United States Patent
Ghim

(10) Patent No.: US 6,964,570 B2
(45) Date of Patent: Nov. 15, 2005

(54) DENTAL LIP RETRACTOR

(76) Inventor: Steven H. Ghim, 8613 Fox Chase La., Charlotte, NC (US) 28269

( * ) Notice: Subject to any disclaimer, the term of this patent is extended or adjusted under 35 U.S.C. 154(b) by 10 days.

(21) Appl. No.: 10/389,585

(22) Filed: Mar. 17, 2003

(65) Prior Publication Data

US 2004/0185415 A1 Sep. 23, 2004

(51) Int. Cl.$^7$ .................................................. A61C 5/00
(52) U.S. Cl. ....................................................... 433/140
(58) Field of Search .................... 433/140; 132/319; 600/237, 238, 239, 242, 240

(56) References Cited

U.S. PATENT DOCUMENTS

| | | | | |
|---|---|---|---|---|
| 278,520 | A | * | 5/1883 | Doyle ........................ 600/242 |
| 548,817 | A | | 10/1895 | Platt |
| 730,184 | A | | 6/1903 | Witter |
| 744,204 | A | | 11/1903 | Jordan |
| 1,009,551 | A | * | 11/1911 | Nations ....................... 600/242 |
| 1,465,259 | A | * | 8/1923 | Friedman .................... 600/227 |
| 1,474,497 | A | | 11/1923 | Stolper |
| 1,959,508 | A | | 5/1934 | Sweet |
| 2,125,980 | A | | 3/1938 | Basil |
| 3,863,627 | A | * | 2/1975 | Bouffard ..................... 600/210 |
| 4,735,569 | A | | 4/1988 | Munk |
| 4,889,490 | A | | 12/1989 | Jenkinson |
| 5,037,298 | A | | 8/1991 | Hickham |
| 5,115,799 | A | * | 5/1992 | McGann ..................... 600/242 |
| 5,513,985 | A | | 5/1996 | Robertson |
| 5,730,597 | A | | 3/1998 | Luttrell |
| 6,102,701 | A | | 8/2000 | Engeron |
| 6,575,749 | B1 | * | 6/2003 | Greenwald .................. 433/141 |
| 6,752,630 | B2 | * | 6/2004 | Roetzer ...................... 433/140 |
| 2002/0124865 | A1 | * | 9/2002 | Davis .......................... 132/319 |

FOREIGN PATENT DOCUMENTS

DE 3202270 A1 8/1983

OTHER PUBLICATIONS

Zila Dental Supply Brochure, May 1–Oct. 31, 2000, The Supply House, p. 255.

* cited by examiner

Primary Examiner—Todd E. Manahan
(74) Attorney, Agent, or Firm—Jung Ho Kim

(57) ABSTRACT

A dental retractor comprising a substantially U-shaped strip and an elongated handle. The U-shaped strip has a top edge and a bottom edge. Each of the top and bottom edges forms a substantially U-shape, wherein the U-shape formed by the bottom edge is smaller than the U-shape formed by the top edge. The elongated handle has a distal end of the handle attached to the U-shaped strip at a substantially trough point of the U-shaped strip.

19 Claims, 5 Drawing Sheets

DENTAL LIP RETRACTOR

BACKGROUND OF THE INVENTION

This invention relates to a dental retractor.

Dental retractors have been used in dentistry for various purposes such as aiding in impression taking for crown and bridge prosthetics, intraoral photography, and fillings. They assist the operator by moving away the lips and cheeks of a subject temporarily. The currently available retractors, however, are not patient-friendly, are expensive to make and are not convenient to use. For example, one conventional retractor used in intraoral photography requires two pieces with each having a hook at one end. The two pieces are placed on the lips of the patient so as to curl around the corners of the patient's mouth and the patient is asked to pull on the two pieces sideways while the dentist takes the photo. Such method is an inconvenient way to take this particular photo and poses much apprehension to the patient. Further, the retractor is costly because two separate pulling pieces are required. Therefore, there is a need for an improved dental retractor which is patient-friendly, inexpensive to make and convenient to use.

SUMMARY OF THE INVENTION

A dental retractor comprising a substantially U-shaped strip and an elongated handle. The U-shaped strip has a top edge and a bottom edge. Each of the top and bottom edges forms a substantially U-shape, wherein the U-shape formed by the bottom edge is smaller than the U-shape formed by the top edge. The elongated handle has a distal end of the handle attached to the U-shaped strip at a substantially trough point of the U-shaped strip.

BRIEF DESCRIPTION OF THE DRAWINGS

In order that the present invention may be clearly understood, it will now be described, by way of example, with reference to the accompanied drawings, wherein like numbers indicate the same or similar components, and wherein.

DETAILED DESCRIPTION OF THE INVENTION

Figure 1:
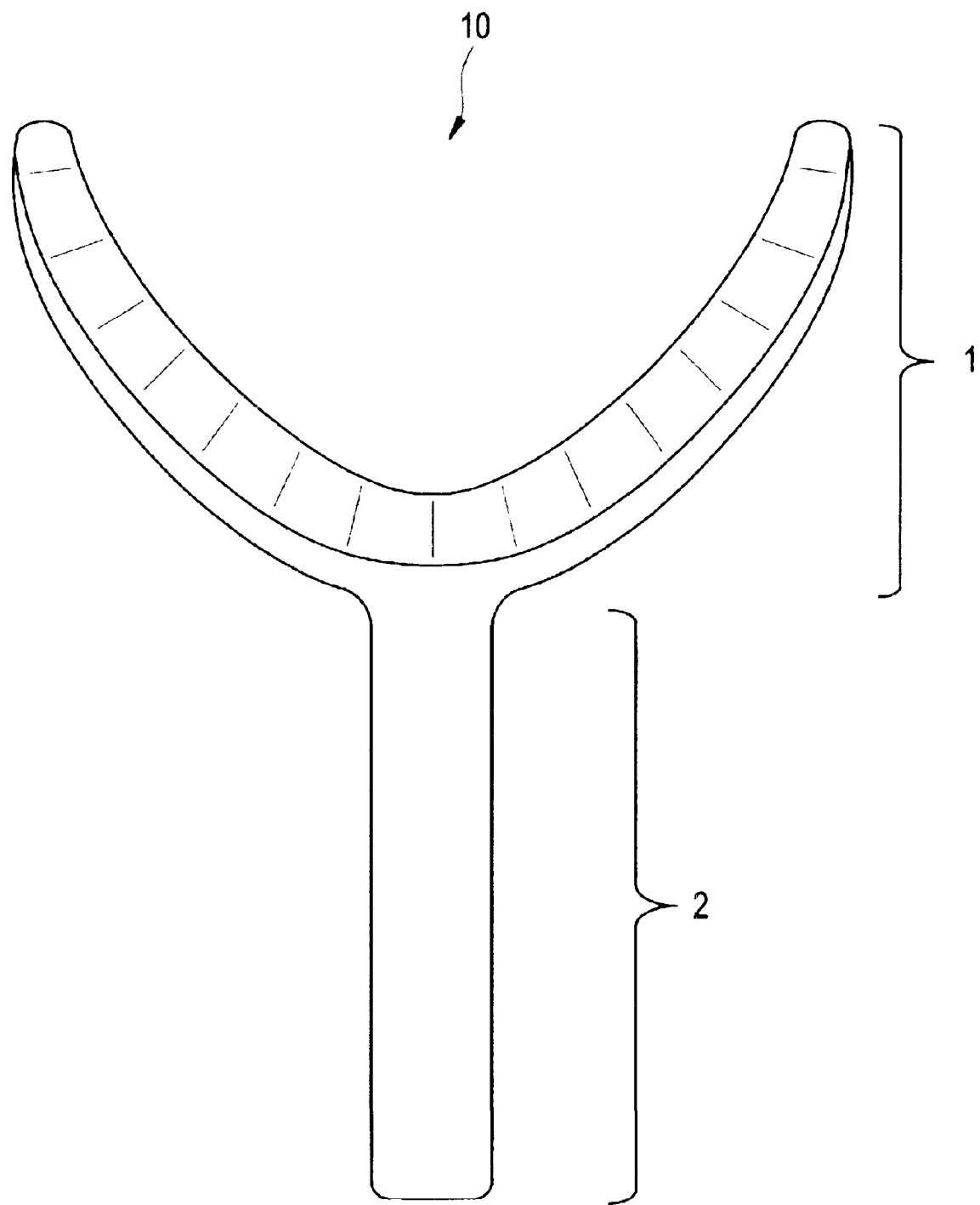
FIG. 1 is a superior view of a retractor according to an embodiment of the present invention.

FIG. 1 discloses a dental retractor 10 according to an embodiment of the present invention. The retractor 10 is comprised of a substantially U-shaped strip 1 and an elongated handle 2.

The substantially U-shaped strip can be of any geometric shape that conforms to an outline surface of a buccal vestibule of a patient's mouth including shapes that are substantially semi-circular, semi-oval, or U-shaped. The U-shaped strip is inserted into the patient's mouth with the U-shaped strip's wings extending sideways along the bottom teeth and/or the upper teeth. The U-shaped strip can be of enough length to cover any number of teeth including 4 to the entire bottom and/or upper teeth. The U-shaped strip has a top edge and a bottom edge, wherein the U-shaped strip forms a substantially inwardly sloping structure as the U-shaped strip extends from the top edge to the bottom edge. The U-shaped strip can slope inwardly continuously or intermittently. The U-shaped strip can even slope outwardly at some points of the extension from the top edge to the bottom edge, but the overall structure remains a substantially inwardly sloping structure. The U-shaped strip can be of any thickness and can have a varying thickness for different parts of the strip as long as the structure has an outer surface with a substantially U-shape. The outer surface of the U-shaped strip is the surface that conforms to an outline surface of a buccal vestibule of a patient's mouth. Each of the top edge and the bottom edge can form a straight line, a curved line, a smooth line, a rough line or any other shaped lines.

The handle 2 can be integrally formed as one piece or formed of plural, separate parts. The handle can form a straight structure, a curved structure, a sharp angled structure, or any other structure that is not straight. The handle can have any cross-section including a circular, oval, rectangular, square, triangular, or any other shaped cross-section that can form a handle. A distal end of the handle 2 can be attached to the U-shaped strip 1 at a substantially trough point of the U-shaped strip 1. The distal end of the handle 2 can also be juxtaposed at a substantially middle section between the top and bottom edges of the U-shaped strip, nearer to the top edge than to the bottom edge of the U-shaped strip or nearer to the bottom edge than to the top edge of the U-shaped strip. A substantially trough point of the U-shaped strip 1 can be any point in proximity to the trough point of the U-shaped strip 1 including points that are distanced from the trough point by about a ⅔ of the way from the trough point to one end of the U-shaped strip 1.

The U-shaped strip 1 and the handle 2 can be integrally formed as one piece in one embodiment. Alternatively, the U-shaped strip 1 can form a separate piece from the handle 2. For example, it can be more economical for the handle 2 to be formed of surgical steel while the U-shaped strip 1 can be removed and disposed. The newly sterile handle piece and a newly replaced U-shaped strip can be used for the next procedure. Still alternatively, the retractor 10 can be formed of two symmetrical parts and a joint section, each part being symmetrical to the other part in reference to a longitudinal axis of the handle. Each of the two symmetrical parts can be formed of plural parts. The advantage of having the two symmetrical parts is that it allows the operator to retract either just one side or two sides of the patient's mouth by using just one or both of the parts, respectively. The decision can be based on the type of the impression being taken or the type of the intraoral photo desired.

When the retractor 10 is formed of plural, separate parts, various fastening methods may be used to interconnect any number of the parts together including screws, male and female connectors, interlocking connectors, a live hinge, glueing, soldering and any other available fastening methods. Any number of the above mentioned fastening methods can be used together in forming the retractor 10. When male and female connectors are used, any number of the male and female connectors can be elongated connectors. When a live hinge is used, two symmetrical parts of the retractor 10, for example, can be connected by a live hinge made up of plastic for attaching the two parts, wherein the live hinge can be a separate piece from the two parts or the live hinge and the two parts can form a one piece structure with the two parts integrally formed on either sides of the live hinge. The benefit of having a live hinge is that the whole structure can be inserted into the patient's vestibule easily when the hinge is collapsed by finger release.

As to materials forming the retractor 10, the U-shaped strip 1 and the handle 2 can be formed from a same material. The U-shaped strip 1 can also be formed of a different material than a material used in forming the handle 2. For example, any or all of the U-shaped strip 1 and the handle 2 can be formed of surgical grade steel. Surgical grade steel (e.g. stainless steel) would be completely sterilizable for use in the operating room setting where sterility of all instruments is required. Alternatively, any or all of the U-shaped strip 1 and the handle 2 can be made of stainless steel base which is coated with a resilient non-metallic material (e.g., sterilizable plastic, rubber or composite material). The non-metallic coating would be more comfortable for the patient. The coated instrument can be strong enough to withstand conventional heat sterilization. As another alternative, any or all of the U-shaped strip 1 and the handle 2 can be entirely formed of a non-metallic material (e.g., sterilizable plastic, rubber or composite material), which is appropriately robust, resilient, and durable, and can be subjected to conventional heat sterilization technique while exhibiting dimensional stability. The composite material can be any composite molding compound including a fiber-filled high temperature thermoplastic resin or a FDA graded and approved polymer such as polyurethane or polyethylene.

In use, the retractor 10 can be inserted inside a buccal vestibule of the mouth of a subject person or animal so that the handle 2 can be pulled forward away from the mouth to retract at least one of a cheek and/or a lip. When the retractor 10 is formed of two symmetrical parts and a joint section with each part being symmetrical to the other part in reference to a longitudinal axis of the handle, the operator can retract either just one side or two sides of the patient's mouth by using just one or both of the parts, respectively. When using just one part of the two symmetrical parts, the operator can retract and pull the retractor in any direction including a forward direction, a side direction, and a diagonal direction.

Figure 2:
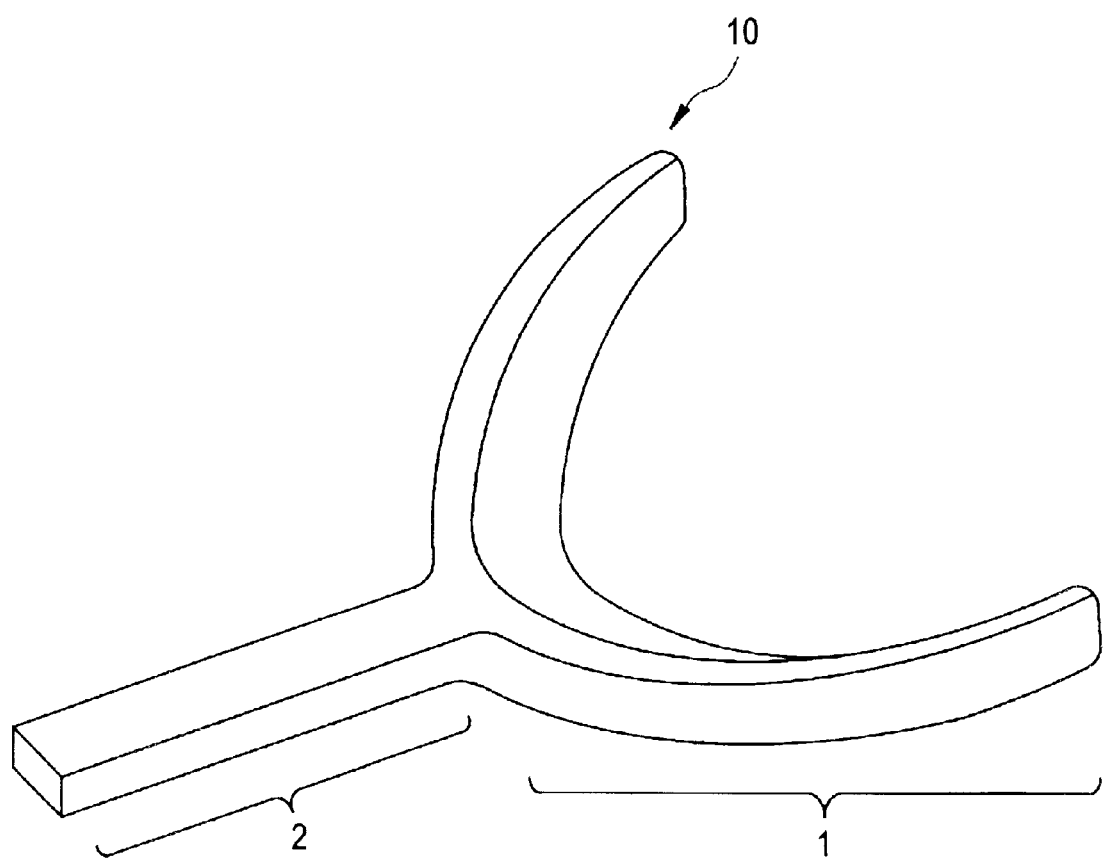
FIG. 2 is a superior-lateral view of the retractor.

FIG. 2 is a superior-lateral view of the retractor 10.

Figure 3:
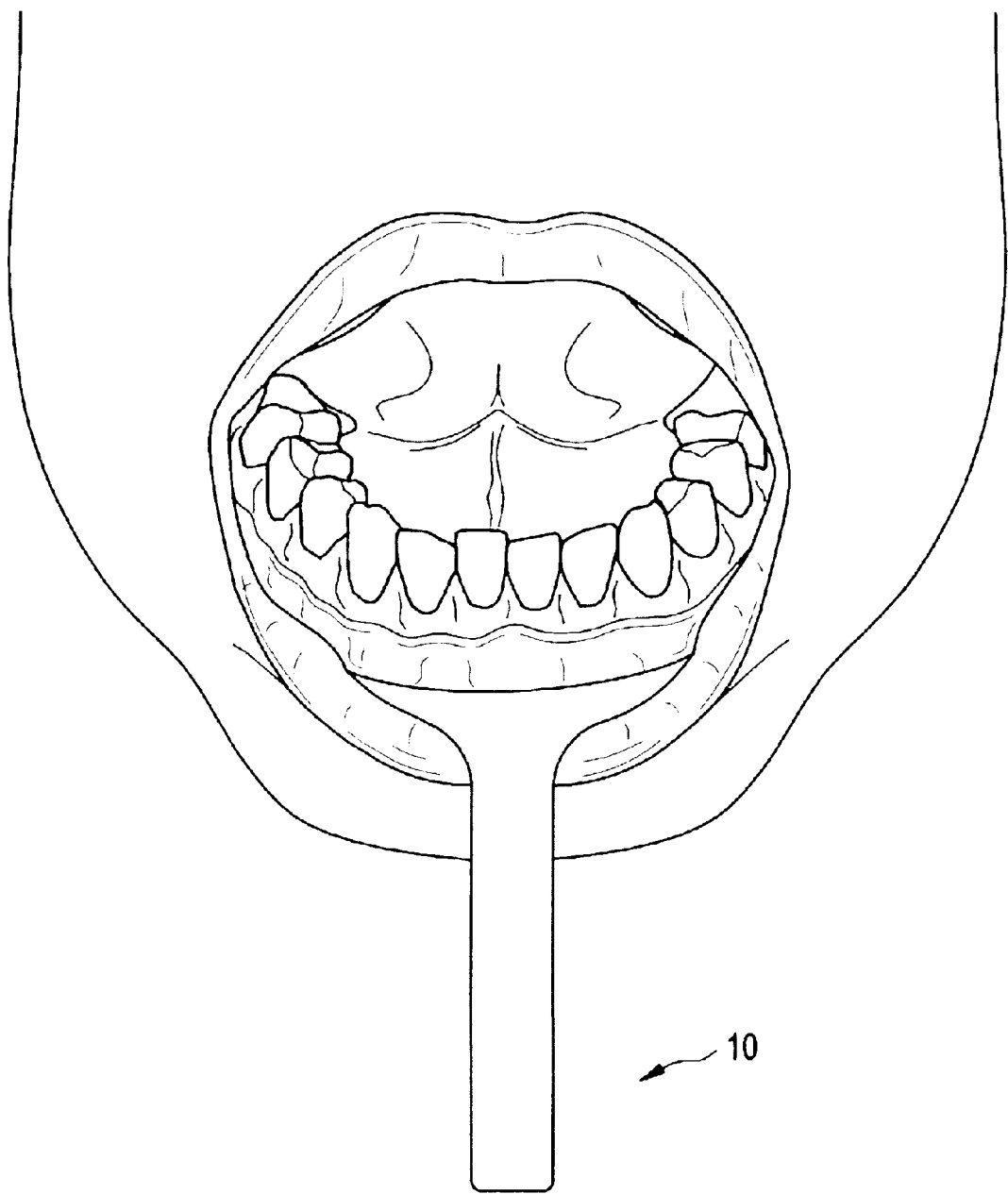
FIG. 3 is a view of the retractor retracting the lower lip of a patient as an illustration of one of the uses for the retractor.

FIG. 3 is a view of the retractor 10 retracting the lower lip of a patient by holding the elongated handle and pulling the elongated handle forward away from the mouth of the patient.

Figure 4:
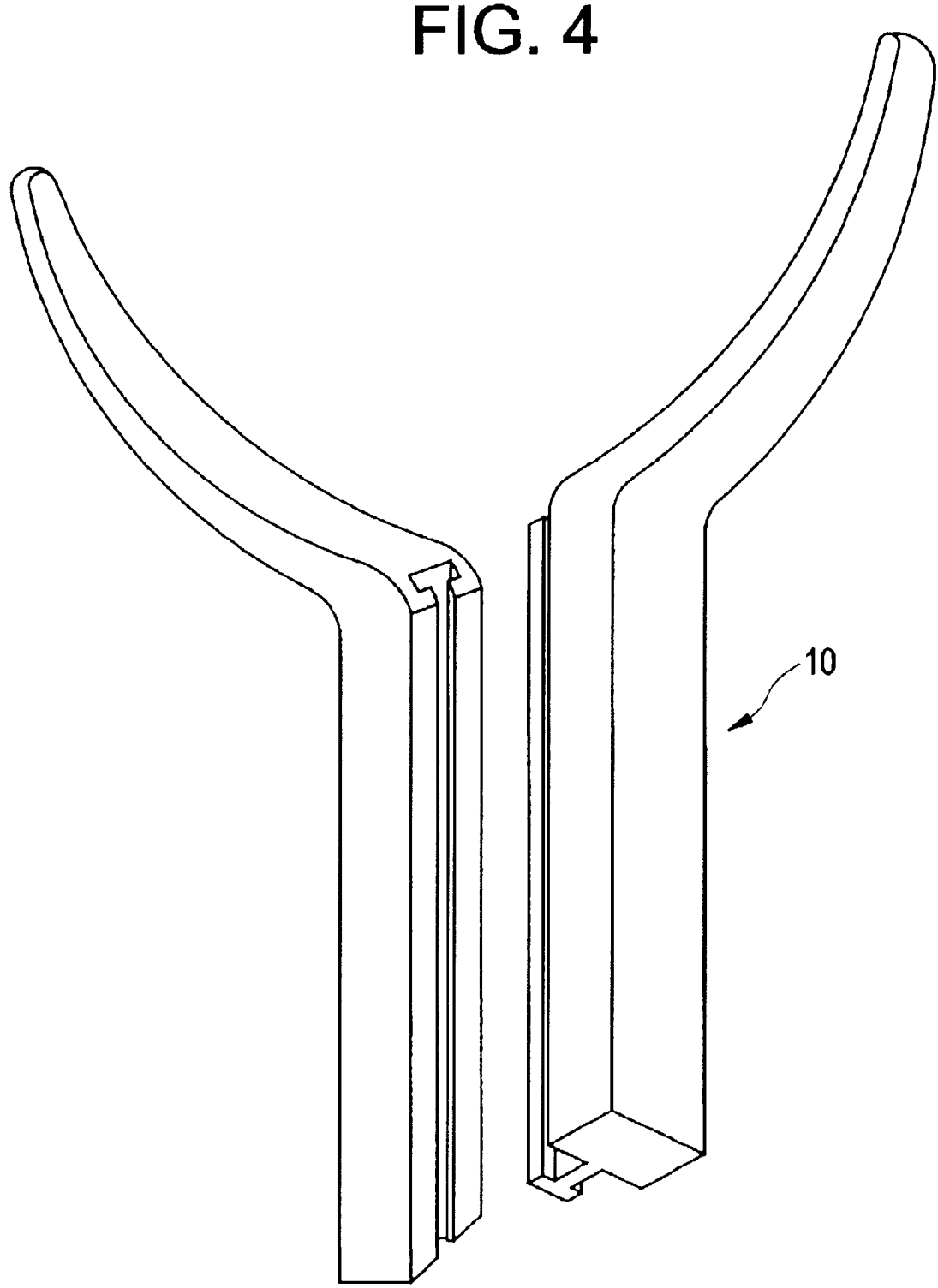
FIG. 4 is a superior view of the retractor having male and female connectors according to an embodiment of the invention.

FIG. 4 discloses the retractor 10 having male and female connectors according to an embodiment of the invention. In another embodiment, the male and female connectors of the FIG. 4 can be replaced with interlocking connectors with one interlocking connector on each piece so that the two separate pieces can be connected by interlocking the connectors of the two pieces.

Figure 5:
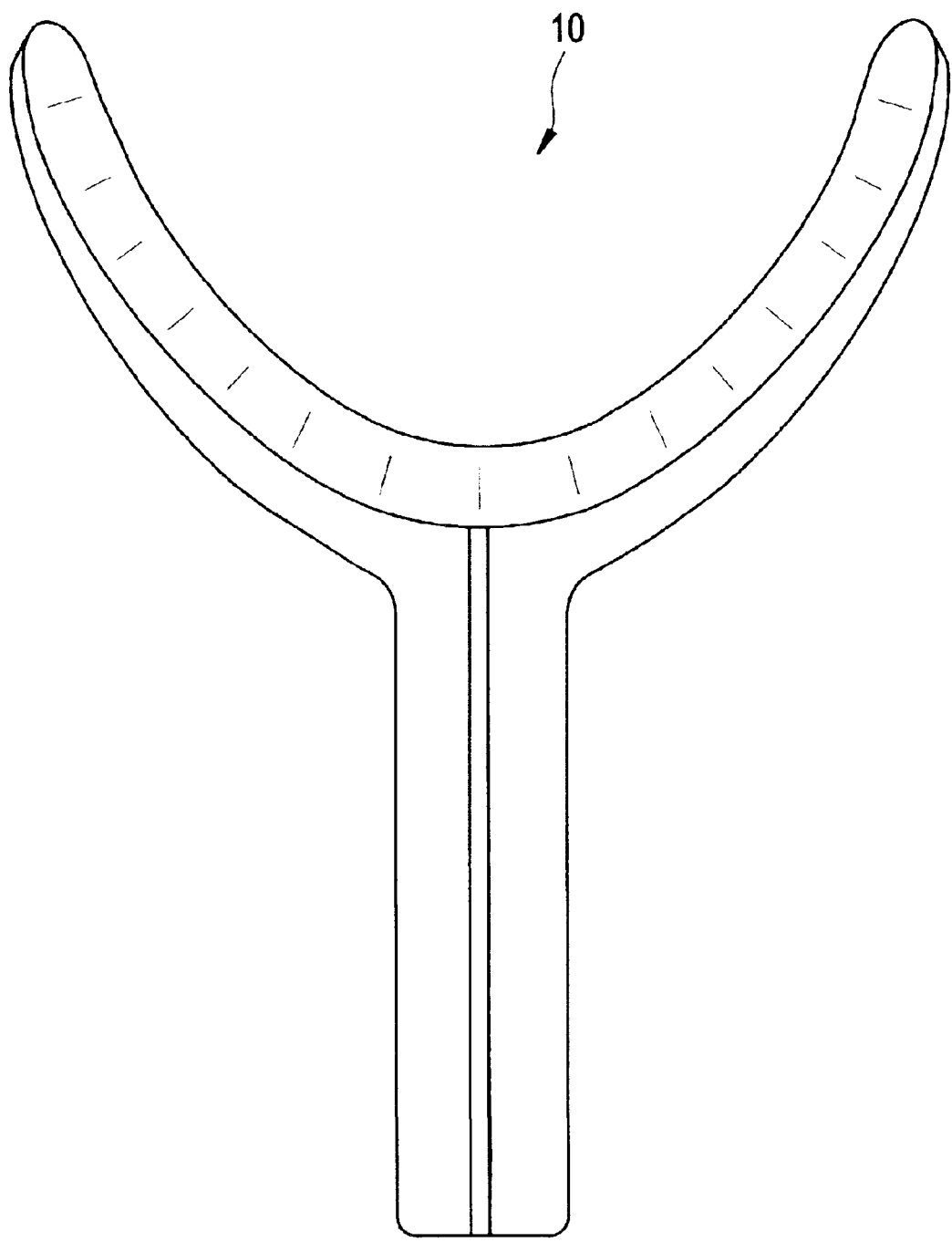
FIG. 5 is a superior view of the retractor having a live hinge according to an embodiment of the invention.

FIG. 5 discloses the retractor 10 having a live hinge according to an embodiment of the invention.

While the invention has been disclosed with reference to certain described embodiments, numerous changes, alteration and modifications to the described embodiments are possible without departing from the spirit and scope of the invention, as defined in the appended claims and equivalents thereof.

What is claimed is:

1. A dental retractor comprising:
    a substantially U-shaped strip having a top edge and a bottom edge, each of the top and bottom edges forming a substantially U-shape, wherein the U-shape formed by the bottom edge is smaller than and is substantially the same in shape as the U-shape formed by the top edge; and
    an elongated handle having a distal end of the handle attached to the U-shaped strip at a substantially trough point of the U-shaped strip, wherein the U-shaped strip forms a substantially inwardly sloping structure as the U-shaped strip extends from the top edge to the bottom edge.

2. The retractor of claim 1, wherein the distal end of the handle is juxtaposed nearer to the top edge than to the bottom edge of the U-shaped strip.

3. The retractor of claim 1, wherein the handle and the U-shaped strip are formed from a same material.

4. The retractor of claim 1, wherein the handle is formed from a different material than a material used in forming the U-shaped strip.

5. The retractor of claim 1, wherein the elongated handle is coupled to the substantially U-shaped strip at an angle to enable insertion of the U-shaped strip inside the mouth of a person and holding and pulling of the elongated handle forward away from the mouth to retract at least one of a cheek and a lip.

6. The retractor of claim 1, wherein the retractor comprises a sterilizable plastic or stainless steel.

7. The retractor of claim 1, wherein the U-shaped strip and the elongated handle are integrally formed as one piece.

8. The retractor of claim 1, wherein the retractor is formed of two symmetrical, separate parts, wherein each part is symmetrical to the other part in reference to a longitudinal axis of the handle and is connected to the other part via a joint section.

9. The retractor of claim 1, wherein the retractor is formed of two symmetrical parts, wherein each part is symmetrical to the other part in reference to a longitudinal axis of the handle and is integrally connected to the other part as one piece via a live hinge.

10. The retractor of claim 1, wherein the elongated handle is not a straight structure.

11. A dental retractor comprising:
    a substantially U-shaped strip having a top edge and a bottom edge, each of the top and bottom edges forming a substantially U-shape, wherein the U-shaped strip forms a substantially inwardly sloping structure as the U-shaped strip extends from the top edge to the bottom edge; and
    an elongated handle having a distal end of the handle attached to the U-shaped strip at a substantially trough point of the U-shaped strip.

12. The retractor of claim 11, wherein the distal end of the handle is juxtaposed nearer to the top edge than to the bottom edge of the U-shaped strip.

13. The retractor of claim 11, wherein the retractor comprises a sterilizable plastic or stainless steel.

14. The retractor of claim 11, wherein the U-shaped strip and the elongated handle are integrally formed as one piece.

15. The retractor of claim 11, wherein the retractor is formed of two symmetrical, separate parts, wherein each part is symmetrical to the other part in reference to a longitudinal axis of the handle and is connected to the other part via a joint section.

16. The retractor of claim 11, wherein the elongated handle is coupled to the U-shaped strip at an angle to enable insertion of the U-shaped strip inside the mouth of a person and holding and pulling of the elongated handle forward away from the mouth to retract at least one of a cheek and a lip.

17. A method of using a dental retractor comprising the steps of:
- inserting a dental retractor inside a buccal vestibule of the mouth of a subject, wherein the dental retractor comprises:
    - a substantially U-shaped strip having a top edge and a bottom edge, each of the top and bottom edges forming a substantially U-shape, wherein the U-shaped strip forms a substantially inwardly sloping structure as the U-shaped strip extends from the top edge to the bottom edge; and
    - an elongated handle having a distal end of the handle attached to the U-shaped strip at a substantially trough point of the U-shaped strip; and
- holding the elongated handle and pulling the elongated handle forward away from the mouth to retract at least one of a cheek and a lip.

18. The method of claim 17, wherein the distal end of the handle is juxtaposed nearer to the top edge than to the bottom edge of the U-shaped strip.

19. The retractor of claim 17, wherein the retractor is formed of two symmetrical, separate parts, wherein each part is symmetrical to the other part in reference to a longitudinal axis of the handle and is connected to the other part via a joint section.

* * * * *